United States Patent [19]

Gordon

[11] Patent Number: 4,829,984

[45] Date of Patent: May 16, 1989

[54] METHOD FOR THE IMPROVEMENT OF TRANSPLANTATION TECHNIQUES AND FOR THE PRESERVATION OF TISSUE

[76] Inventor: Robert T. Gordon, 4936 West Estes, Skokie, Ill. 60077

[21] Appl. No.: 936,321

[22] Filed: Dec. 1, 1986

Related U.S. Application Data

[63] Continuation-in-part of Ser. No. 561,811, Dec. 15, 1983, abandoned.

[51] Int. Cl.$^4$ ............................................. A61B 19/00
[52] U.S. Cl. ........................................ 600/12; 600/9; 424/617
[58] Field of Search ...................... 128/1.1, 1.3, 804; 424/131–147

[56] References Cited

U.S. PATENT DOCUMENTS

| | | | |
|---|---|---|---|
| 4,106,488 | 8/1978 | Gordon | 600/10 |
| 4,269,826 | 5/1981 | Zimmermann et al. | 424/101 |
| 4,359,453 | 11/1982 | Gordon | 424/1.1 |
| 4,758,429 | 7/1988 | Gordon | 128/1.3 X |

*Primary Examiner*—Francis Jaworski
*Attorney, Agent, or Firm*—Scully, Scott, Murphy & Presser

[57] ABSTRACT

The present invention relates to a process for improvement and enhancement of transplantation by the introduction of particles to the tissue area where rejection may occur. The tissue is then subjected to a constant magnetic field thereby affecting the metabolism of the cells therein. Also contemplated is the use of a constant magnetic field to effect naturally occurring paramagnetic or ferromagnetic components in the cells of tissue during transplantation.

32 Claims, No Drawings

METHOD FOR THE IMPROVEMENT OF TRANSPLANTATION TECHNIQUES AND FOR THE PRESERVATION OF TISSUE

This application is continuation-in-part of application Ser. No. 561,811 filed Dec. 15, 1983, and now abandoned.

FIELD OF THE INVENTION

This invention relates to a method for the improvement of transplantation through alteration of the rejection process and a means for the preservation of tissue.

BACKGROUND OF THE INVENTION

The current state of transplantation is limited by two essential problems. The first problem relates to the process of rejection which occurs to some extent in most transplants. The second problem involves the preservation of tissue both donor's and recipient's.

The process of rejection is related to the immunological properties of the recipient's and donor's tissue. These immunological properties can be divided into two areas; antibody-mediated humoral group and the cellular-mediated mechanisms. Humoral immunity involves antibody produced by B-lymphocytes. This antibody when combined with the antigen can lyse cells and tissues, produce inflammation, bind cytotoxic lymphocytes or alter the function of the tissue. The antibody can bind antigen and activate the complement system which produces and releases substances which attract inflammatory cells and increase vascular permeability. Phagocytic cells can bind to these substances and are activated to cause tissue destruction. In addition, the antibodies may bind to the tissue involved and inhibit function of that tissue. Some antibodies bind to an antigen or cell and attract a K-lymphocyte which destroys the antibody bound cell. This process is known as antibody-dependent cellular cytotoxicity.

Cellular immunity involves T-lymphocytes which when activated can destroy tissue. There are both helper and suppressor lymphocytes. The helper lymphocytes promote immunologic reactions while the suppressor lymphocytes impede these reactions. There also exist natural killer lymphocytes which also play a role in the rejection process.

In addition, in both the host and the recipient, the macrophages and other phagocytic cells aid the rejection process by assisting the antibody mediated and cellular mediated mechanisms.

There exist a number of methods to monitor the rejection process. The serum of the recipient is mixed with lymphocytes from the donor in the presence of complement to detect the presence of antibodies. Trypan blue and ethidium bromide tests have been used to detect cytotoxic antibodies. Other tests have been used to evaluate the lymphocyte populations in tissues. Immunologic studies include: lymphocyte mediated cyctotoxicity, complement dependent cytotoxicity, spontaneous blastogenesis, as well as myocardial biopsy. A number of other studies are currently used to try to monitor the rejection process. However, attempts to monitor and prevent or treat the rejection process have met with great difficulty. Consequently, it is the purpose of this instant invention to improve the process of transplantation.

In addition, attempts at preservation of the donor and recipient have gone through many stages. Initially perfusion of blood or immersion in ice was used for the tissue. Currently methods utilize cooling with agents to decrease the metabolism of the cells, i.e. cardiplegic solutions in cardiac allografts. However, preservation is limited at this time to 4–24 hours. The purpose of this instant invention is also to prolong the time and to increase the quality of tissue preservation.

BRIEF DESCRIPTION OF THE INVENTION

The instant invention relates to a method for the alteration and improvement of transplantation techniques with the use of particles and a constant electromagnetic field to affect the rejection process. In addition, this invention relates to the use of magnetic fields to enhance tissue preservation.

DETAILED DESCRIPTION OF THE INVENTION

In attempts to overcome the rejection process, a number of approaches have previously been taken. Prevention of rejection is tried by matching of the donor and the recipient via the antigens present; ABO blood group match is essentially HLA and HLA-DR matches are also attempted. While possibly helping the matching techniques, these methods do not uniformly prevent rejection.

An effort to treat rejection involves the use of drugs such as cyclosporine, azathioprine, prednisone, antilymphocyte globulin, etc. While these drugs do suppress the immunological process, they also expose the host to a large number of complications. These complications include; massive infections bacterial and fungal, renal toxicity, and depression of other normal body functions. Cyclosporine has been associated with an increased incidence in lymphomas, as well (D. L. Modry M.D., et al., pgs. 122–135, and Robert P. Lanza, B.A., et al., pgs. 151–154, In: Heart Transplantation, 3rd Annual Scientific Session, Int'l Soc. for Heart Transplantation, Prof. Med. Services, Div. Prof. Lab. Services, Inc., Ridgewood, N.J., Vol. 11, No. 2, Feb., 1983)) (Ivan Hilgert, Ph.D., pgs. 192–196, In: Heart Transplantation, Prof. Med. Services, Div. Prof. Lab. Services Inc., Ridgewood, N.J., Vol. 11, No. 3, May, 1983)).

The endocardial biopsy technique is the best technique for following rejection. The histologic picture of lymphocyte infiltration and other changes is characteristic. Other parameters such as EKG voltage, atrial arrythmias, heart sounds, etc. do not correlate well with rejection especially when cyclosporine is used. The on-going rejection process is often seen as progressive atherosclerosis in the donor coronary arteries thought to be secondary to an immunological response.

Further attempts to modify the rejection process have included pre-transplant blood transfusions, irradiation of the graft and/or recipient, thoracic duct drainage and the use of lectins to induce tolerance (D. K. C. Cooper, M.B., Ph.D., et al., pgs. 104–110, In: Heart Transplantation, 3rd Annual Scientific Session, Int'l Soc. for Heart Transplantation, Prof. Med. Services, Div. Prof. Lab. Services, Inc., Ridgewood, N.J., Vol. 11, No. 2, Feb., 1983)) (V. I. Shumakov, et al., pgs. 281–286, In: Heart Transplantation, Prof. Med. Services, Div. Prof. Lab. Services, Inc., Ridgewood, N.J., Vol. 11, No. 4, August, 1983)) (Mary C. Mancini, M.D., et al., pgs. 175–180, In: Heart Transplantation, Prof. Med. Services, Div. Prof. Lab. Services, Inc., Ridgewood, N.J., Vol. 11, No. 3, May, 1983)). However, all these methods have not solved the problem of rejection.

Current methods of tissue preservation include: perfusion with oxygenated substrates, topical cooling, use of agents to decrease the rate of metabolism and perfusion with cold solutions to preserve the tissue. Attempts to preserve the heart have provided means over a period from 4–24 hours; however, alterations in tissue function still occur. No good satisfactory means of lung preservation now exist either with topical cooling or with perfusion of cooling solutions. The problem exists even with cooling that metabolism of the myocardial cells still takes place with a continual decrease in energy stores and function. Systems to preserve tissue include: the use of pharmacologic agents to conserve high energy phosphates or to attempt to increase them prior to transplantation. All these approaches have not been able to extend preservation beyond 24 hours and still maintain tissue function.

The instant invention relates to a method for the improvement of the transplantation process. Through the application of this process, particles which are ferromagnetic, paramagnetic, or diamagnetic are introduced into the donor tissue either prior to, during, or after ex-plantation. These particles may be introduced intravenously, intra-arterially, intra-lymphatically, and/or via local perfusion. The particles are then taken up by the macrophages, phagocytic cells, and other cells of the immunological system which are contributory to the rejection process. An alternating electromagnetic field is then applied in the range from 1 hertz to 100 megahertz. Energy is transmitted to these cells and the immunological reaction greatly inhibited.

A wide range of ferromagnetic, paramagnetic and diamagnetic particles which possess enhanced magnetic characteristics and in combination with desirable structural properties are particularly useful in light of the applications described in this instant invention.

Whereas the particles described in U.S. Pat. Nos. 4,106,488 and 4,303,636 were selected primarily on the basis of their size and their ability to be inductively heated; it is appreciated that additional criteria must be considered when selecting a particle for a particular application. In selecting the particles of the instant invention the following magnetic and physical characteristics were evaluated: Magnetic permeability, magnetic susceptibility, magnetic moment, Curie points, and thermal conductivity. Magnetic permeability is a property of materials modifying the action of magnetic poles placed therein and modifying the magnetic induction resulting when the material is subjected to a magnetic field and may be defined as the ratio of the magnetic induction in the substance to the magnetizing field to which it is subjected. Magnetic susceptibility is measured by the ratio of the intensity of magnetization produced in a substance to the magnetizing force or intensity of the field to which it is subjected. Magnetic moment is measured by the torque experienced when it is at right angle to a uniform field of unit intensity. The value for magnetic moment is given by the product of the magnetic pole strength by the distance between the two poles. The Curie point represents the temperature above which substances lose their ferromagnetic properties. Thermal conductivity relates to the ability of a substance to transfer thermal energy and is known to be effective by temperature.

In addition to the physical and magnetic characteristics listed above, other parameters must be evaluated. For ease of consideration these additional parameters may be grouped in relation to the time course of treatment. For example certain evaluations as to the efficacy of a particular particle can be made prior to the introduction of said particle to the subject of interest, but such a selection must be modified by considerations relating to the behavior of the particle during the treatment period, desirable structural properties, and finally consideration must also be given to post-treatment parameters.

Pre-treatment parameters to be considered comprise, an evaluation of the magnetic and physical and structural properties of the particles, the composition and solution properties displayed by the particles, and route of administration of said particles. For example, if the particles are to be delivered by intravenous injection it would be important for the particles to be in a stable colloidal suspension in aqueous media, or any other media of solution compatible to the procedures for improvement in methods of transplantation through alteration of the rejection process and a means for improving and enhancing the preservation of tissue in this instant invention.

After introduction of the particles into the subject of interest and/or organ of transplant, the following parameters become important: biocompatibility and toxicity considerations, the rate and degree of cellular uptake of the particles, the specificity of said uptake, the sub-cellular localization of particles once they have been taken up by the cells, the modification of the magnetic properties and structural properties as a result of intra-cellular localization, and the effect upon magnetic properties and structural properties as a result of metabolic activity within the cells. For example, surfactants may be profitably employed to reduce surface tension, and mask groups contributing to zeta potentials thereby enhancing the uptake of particles by the cells. In reference to sub-cellular localization it is possible to specifically target particles to specific intracellular locales by constructing the particle in the form of a molecular analog (e.g., mimic) of an endogenous compartmentalized cellular component. For example by forming particles containing prophyrin moieties and providing same to cells within the treatment area; the particles will accumulate within prophyrin-rich area within the cells, i.e., mitochondria or chloroplasts, and participate in the cellular reactions attendant thereto.

It is important to realize that as the structural complexity of the particle increases not only is size a consideration but also the overall shape and the conformation and configuration of various particle components must be considered. With reference to the porphyrin-containing particles mentioned above, it is known, for example, that the position of the metal value relative to the plane of the porphyrin ring has important consequences with respect to the metal's reactive properties. Further it must be appreciated that the type and position of the side chains on the porphyrin moiety can act to position the metal in a particular orientation and as a corollary, the metal will have an affect of the conformation of the side chains of the porphyrin as well.

The interactions at the particle surface-cellular environment interface are also important. For example, induced magnetic moments can result from the ordering which takes place at the particle surface.

Further particles which are subject to cellular metabolism will display a change in magnetic characteristic as a result of said metabolism. This change in magnetic character of the particles in the donor and recipient can be used to monitor the state of the rejection process.

Although the intracellular effects upon metabolizable, organic metal containing-particles as described above are important considerations it should be remembered that the characteristics of less complex particles also affected by intracellular localization. For example, the inductive heating of the particles comprised of inorganic materials in suspension outside the cell; generally transmit their effect through hysteresis owing to their small size. However, after uptake of cells the individual particles tend to cluster providing an overall "group" particle size whereby heating due to eddy currents is also possible.

Finally, with respect to post-treatment practice, consideration must be given to the removal of the particles from the subject of interest and/or organ of transplant. The removal is accomplished by natural excretory processes which may be supplemented with chelating agents or metal efflux stimulating compositions.

Particularly useful particles include both inorganic elements and compounds as well as metal containing organic compounds. Inorganic elements and compounds particularly well suited, owing to their favorable magnetic parameters, comprise elements, such as dysprosium, erbium, europium, gadolinium, holmium, samarium, terbium, thulium, ytterbium or yttrium and compounds thereof such as dysprosium sulfate, erbium sulfate, europium oxide, europium sulfate, gadolinium oxide, gadolinium sulfate, holmium oxide, samarium sulfate, terbium oxide, terbium sulfate, thulium oxide, ytterbium sulfide, yttrium oxide, yttrium sulfate, yttrium ferrioxide ($Y_3Fe_5O_{12}$), yttrium aluminum oxide ($Y_3Al_5O_{12}$), other dimetallic compounds such as dysprosium-nickel, dysprosium-cobalt, gadolinium-iron, ytterbium-iron, cobalt-samarium, gadolinium-yttrium, and dysprosium-gallium, and actinide series elements and compounds thereof.

Metal containing-organic molecules useful for the application discussed above, comprise particles of iron-dextrans such as FeOOH-dextran complexes and other dextran metal complexes wherein the metal is selected from the group comprising cobalt, zinc, chromium, nickel, gallium, platinum, manganese and rare earth metals such as dyprosium, erbium, europium, gadolinium holmium, samarium, terbium, thulium, ytterbium and yttrium, other dimetallic compounds such as dysprosium-nickel, dysprosium-cobalt, gadolinium-iron, ytterbium-iron, cobalt-samarium, gadolinium-yttrium, and hysprosium-gallium, actinide series elements and compounds, ferric ammonium citrate, and various iron transporting and chelating compounds such as enterochelin, hydroxamates, phenolates, ferrichromes, desferri-ferrichromes, ferritin, ferric mycobactins, and iron-sulfur proteins such as ferredoxin and rubredoxin and transferrin as well as transferrin compounds and complexes.

Particularly appropriate metal-containing organic structures for use with the present invention are the porphyrins such as etioporphyrins, mesoporphyrins, uroporphyrins, coproporphyrins, protoporphyrins, and dicarboxylic acid containing porphyrins and substituted porphyrins such as tetraphenylporphyrin sulfonate (TPPS). Especially advantageous protoporphyrins comprise hematoporphyrins, chlorophylls, and cytochromes. In addition to the naturally occurring protoporphyrins which possess either iron or magnesium containing moieties, mixed-metal or di-metal hybrid porphyrins may also be prepared. For example, by substituting an alternative metal for the iron in hematoporphyrin, the advantages of the porphyrin moiety (e.g., in terms of specificity of localization is retained while the unique magnetic properties of the new metal enhance the sensitivity of the substituted molecule. Suitable metals for purposes of substitution comprise cobalt, manganeses, zinc, chromium, gallium, nickel, platinum and rare earth series of metals dysprosium, erbium, europium, gadolinium holmium, samarium, terbium, thulium, ytterbium and ytterium, dimetlllic compounds such as dysprosium-nickel, dysprosium-cobalt, gadolinium-iron, ytterbium-iron, cobalt-samarium, gadolinium-yttrium, dysprosium-gallium and actinide series elements and compounds thereof. The substituted porphyrins are then optionally reacted with dextran to form a metal-containing porphyrin dextran complex in particle form. Suitable porphyrin acceptors comprise any dicarboxylic acid containing porphyrin, such as protoporphyrins (e.g., hematoporphyrins) and the like.

The substitution reaction is carried out in vitro by reacting the desired metal with the desired porphyrin in the presence of the enzyme ferrochelatase (E.C. 4.11.1.1). Reaction conditions as described by Jones and Jones (Biochem. J. 113:507–14 (1969)) or Honeybourne, et al. (FEBS Lett.: 98:207 ∝ 210 (1979)) are suitable.

Additional particle systems particularly suited to use in this instant invention include $Fe_3O_4$-transferrin dextran, metal-transferrin (transition, rare-earth), metalloporphyrin-transferrin, Antibody-ferritin-particles, Antibody-ferritin-transferrin particles, Antibody-transferrin-particles. Metal-porphyrin-metal complexes, Metallothionein particles, and Lectin particles. Useful particle systems for use in this instant invention further comprise: Where particle=$Fe_3O_4$, Transition Metal, Rare-earth metal, Metalloporphyrin, etc. as well as Ferromagnetic and Paramagnetic particles.

One magnetic characteristic know to be temperature dependent is magnetic susceptibility. Magnetic susceptibility is measured by the ratio of the intensity of magnetization produced in a substance to the magnetizing force or intensity of the field to which it is subjected. This magnetic characteristic is routinely measured by magnetometer devices, such as a vibrating magnetometer or a flux gate magnetometer. Therefore, by measuring the magnetic susceptibility of particles at various temperatures, it is quite simple to calibrate the magnetometer equipment so that when it measures the magnetic susceptibility of the particles a simple calibration will indicate the exact corresponding temperature of the particle.

By way of illustrating the increased magnetic susceptibility of some of the elements or compounds described above, the following table is provided:

| Element or Compound | Temp (K.) | Mag. Sus.($10^6$ cgs) |
|---|---|---|
| Iron Oxide (ref.) | 293 | +7,200 |
| Dysprosium Oxide | 287.2 | +89,600 |
| Dysprosium Sulfate Octahydrate | 291.2 | +92,760 |
| Erbium Oxide | 286 | +73,920 |
| Erbium Sulfate Octahydrate | 293 | +74,600 |
| Europium | 293 | +34,000 |
| Europium Oxide | 298 | +10,100 |
| Europium Sulfate | 293 | +25,730 |
| Holmium Oxide | 293 | +88,100 |
| Holmium Sulfate Octahydrate | 293 | +91,600 |
| Terbium | 273 | +146,000 |
| Terbium Oxide | 288.1 | +78,340 |
| Terbium Sulfate Octahydrate | 293 | +76,500 |
| Thulium | 291 | +25,500 |

| Element or Compound | Temp (K.) | Mag. Sus.($10^6$ cgs) |
|---|---|---|
| Thulium | 296.5 | +51,444 |
| Ytterbium Sulfide | 292 | +18,300 |

Thus, the enhanced magnetic characteristics displayed by the particles of the subject invention results in an increase in an electromagnetic field thereby increasing the overall sensitivity and control of the modalities for the improvement of transplantation techniques and for the preservation of tissue as described in this instant invention.

A further benefit is derived from the fact that some particle compositions comprise a ferromagnetic, paramagnetic, or diamagnetic component integrated into a cell or organelle specific molecular structure, thereby permitting efficient targeting and delivery of said particles to specific intracellular compartments such as mitochondria, chloroplasts, nuclei, vacuoles, and the like.

The inductive heating of minute particles selected from the above described list and/or compounds and complexes thereof, and introduced intravenously, intra-arterially, intra-lymphatically, or via local perfusion in the subject of interest, donor, recipient, and/or organ of transplant, is achieved by using an electronic oscillator operating in the high-frequency range 1 hertz to 100 megahertz which heats the particles by subjecting them to an intense high-frequency field within a large but otherwise conventional helical coil, field energy being converted to heat through hysteresis losses and the resistive dissipation of eddy currents. The helical inductive coil is of sufficient internal diameter to permit the donor and/or the recipient to pass within and of such length to encompass the length of the donor and/or the recipient. Generally, the internal diameter should be at least 2 feet, but preferably would be greater than 3-6 feet in diameter. No maximum diameter is known to exist except that required from practical and economical considerations. Diameters of inductive coils of greater than 6 feet have a preferential effect in the overall process by providing more uniform flux gradient to the donor and/or the recipient.

The frequency of the electromagnetic alternating high frequency field will range from 1 hertz to 100 megahertz and the power input of the oscillator-generator will range from 0.5 kilowatts per kg. of subject's body weight 0.75 kilowatts of power per 1.0 kilograms of body weight has been found to be particularly useful. In this power and frequency range, the coil is selected to produce from 200-1000 oersteds, preferably 550-650 oersteds, but may function from 100-70,000 oersteds, as well as other variations.

The time necessary to inductively heat the minute particles held within the cells to be treated depends substantially upon the frequency and the power producing the alternating electromagnetic field and ultimately the strength of the field produced. In general, it has been found that subjecting th subject to 5 to 12 minutes or preferably 8 to 10 minutes of the alternating electromagnetic field would be adequate to bring about the necessary temperature rise of approximately 9.0° Centigrade and that the variables with respect to the type and concentration of the particles in the vehicle and the electromagnetic treatment are not critical provided that the necessary temperature is achieved. In further embodiment, since the instant invention provides the possibilities for specific particle distribution and a sensing of the responsiveness to the various treatment fields, high temperature treatment modalities are also possible. The 9.0° Centigrade temperature rise as discussed supra is, of course, predicated on the situation in which particle distribution, magnetic state, and orientation were equal in all cells under the treatment conditions. However, employing the methods of this instant invention thereby affecting specific particle distribution, orientation, differential magnetic susceptibility, timing and other parameters described herein, within cells in the target area, increases in the intracellular temperature up to 100° Centigrade are possible without substantially damaging surrounding tissues and cells.

Biological alterations are induced by the energy input to the particle and thereupon to the interior of the cell. Thus the same energy input may be accomplished by application over a long period of time with a consistent small temperature rise for 10-20 minutes or when the same total amount of energy is applied over a short period of time a higher temperature results (100° C. for a few seconds). Obviously, timing and energy parameters may be adjusted to provide a spectrum of intracellular temperature which may be utilized in this instant invention depending upon the treatment appropriate in specific cases.

In a further embodiment of this instant invention, the particles introduced either intravenously, intra-arterially, intra-lymphatically and/or locally as described above may be used as a method of delivering agents primarily to the interior of the subject's cells by having the agent encapsulated within said particles and released at the proper time by application of the high frequency alternating electromagnetic field thus solubilizing the said particles within the cells of the subject.

A further embodiment of this instant invention involves the introduction of the particles to the recipient either prior to, during, and/or after transplantation. The particles are taken up by the host macrophages and functional cells of the rejection process. An alternating of magnetic field strength of between about 300 gauss to about 100 kilogauss is then applied to introduce energy to these cells and inhibit their function and/or destroy them. The rejection process in the host is accordingly greatly reduced.

This process can also be used in the post-transplant treatment of the recipient's rejection. When rejection begins one of the first signs is an increase in the local endothelial permeability with edema formation (Gregory E. Scott, M.D., et al., pgs. 232-236, In: Heart Transplantation, Int'l Soc. for Heart Transplantation, Prof. Med. Services, Div. Prof. Lab Services, Inc., Ridgewood, N.J. Vol. 11, No. 3, May, 1983)). This edema formation is a good monitor of the rejection process. Consequently, by the introduction of the particles either intravenously, intra-arterially, intra-lyphatically and/or locally, the particles may be released locally in the exact location where the rejection is occurring. Then an alternating electromagnetic field may be applied to inhibit the rejection process in the exact location where the rejection and inflammation is occurring. A localized magnetic field ay also be used to further guide the particles to the transplant's site.

Tissue preservation may be achieved through the use of a constant strength strong magnetic field to decrease the rate of metabolism and thereby help to preserve the tissue. The magnetic field strength in the order of 300 gauss to 100 kilogauss is recommended. This process may also be used in conjunction with other preservation techniques involving intramuscular perfusion, intravascular cooling, topical cooling, etc. This method may also be used during post-transplantation to enhance graft survival. It is believed that the paramagnetic and ferromagnetic components of the mitochondria of the cells are affected by the magnetic field in the absence of the introduction of particles. The tissue cells are therefore inherently responsive to the magnetic field resulting in a limit in the rise of enzyme levels indicative of the decreased metabolism and a resulting inhibition of mitochondrial swelling.

The use of particles which are ferromagnetic, paramagnetic and diamagnetic, and/or any selection previously described for use in this instant invention, together with a constant electromagnetic field to inhibit the rejection process through the alteration of the immunological mechanism represents an advance in the ability for successful transplantation. In addition, the use of magnetic alterations in the environment of the tissue to prolong survival is of significance in transplantation, cardiac surgery, as well as in other modalities of treatment and procedures.

Various attempts have been made to preserve myocardial tissue during cardiac surgical and transplantation procedures. All current approaches include the use of hypothermia, potassium solutions and calcium channel blockers. All of these efforts involve the chemical approach to decrease the metabolic rate of the cells and in some cases to provide substrate to decrease cellular damage (Fremes S. E., Christakis G. T., Weisel, R. D., et al. (1984), J. Thorac Cardiovasc. Surg. 88:726-741; Lazar H. L., Buckberg G. D., Manganaro A. J., et al. (1980), J. Thorac. Cardiovasc. Surg. 80:350-359; Khuri S. F., Josa M., Marson W., et al. (1983), J. Thorac. Cardiovasc. Surg. 86:667-678).

The following examples are illustrative of the instant invention wherein a constant magnetic field is used to provide myocardial preservation. The method is extendible to other tissues as well.

EXAMPLE I

The following experiments were carried out to test the ability of the instant invention technique in the absence of introduction of particles to repress lipoamide dehydrogenase (LDH) and creatine phosphokinase (CPK) levels in myocardial tissue which normally increase in a donor tissue when removed from the donor. Electron microscopy was used to observe structural differences.

Ten Sprague-Dawley rats were sacrificed and the hearts removed. The aortic root of each animal's heart was perfused with 5 ml of Ringers lactate at 30° C. Five animals in each group received an intravenous injection of $FeTPPS_4$ (Irontetraphenylporphine sulfonate) (8 mg/ml) 0.3 ml, 1 hour prior to sacrifice. Each heart was then divided into four tissue sections and assigned to either Group I or Group II. Each sample was weighed to make sure the mass was uniform and then placed in a tube of 5 ml of Ringers lactate solution. Each section was designed to be as uniform as possible in muscle mass and composition.

In Group I the specimens were kept at 30° C. for 3 hour. However, in Group II the specimens were kept at 30° C. for 1 hour and then exposed to a high intensity constant strength magnetic field of 45 kilogauss (superconducting magnet) for 2 hours. The 5 ml of fluid in each tube was analyzed for creatine phosphokinase (CPK) and lactic dehydrogenase (LDH) levels and the tissues submitted for electron microscopy to evaluate mitochondrial structure.

TABLE I

CPK Levels

| Animal | Group I (Control) | Group II (Treated) | Percent Reduction in Enzyme Level |
|---|---|---|---|
| 1 | 1028 | 440 | 57% |
| 2 | 1776 | 497 | 72% |
| 3 | 2524 | 1576 | 38% |
| 4 | 2111 | 980 | 54% |
| 5 | 1910 | 576 | 70% |
| 6 | 1345 | 501 | 63% |
| 7 | 1542 | 531 | 66% |
| 8 | 1397 | 517 | 63% |
| 9 | 1725 | 625 | 64% |
| 10 | 1640 | 560 | 66% |
| | | | 61% (Average) |

Reduction in Enzyme Levels

| Injected (#6–#10) | 64% |
|---|---|
| Non-Injected (#1–#5) | 58% |

TABLE II

LDH Levels

| Animal | Group I (Control) | Group II (Treated) | Perent Reduction in Enzyme Level |
|---|---|---|---|
| 1 | 930 | 430 | 54% |
| 2 | 1660 | 480 | 71% |
| 3 | 2020 | 1360 | 33% |
| 4 | 2000 | 960 | 52% |
| 5 | 1780 | 550 | 69% |
| 6 | 1020 | 470 | 54% |
| 7 | 1380 | 410 | 70% |
| 8 | 1230 | 430 | 65% |
| 9 | 1630 | 560 | 66% |
| 10 | 1560 | 440 | 72% |
| | | | 61% (Average) |

Reduction in Enzyme Levels

| Injected (#6–#10) | 65% |
|---|---|
| Non-Injected (#1–#5) | 56% |

Each sample group was averaged and compared for each animal with respect to enzyme level (Tables I and II). In each case the enzyme level in the treated group was significantly below that of the control group (61%). Good correlation between the CPK and LDH levels was demonstrated with a 61% reduction ($p<0.001$). Electron microscopy showed good maintenance of mitochondrial structure as compared to the control group with a decrease in the amount of edema present. Slight improvement in the amount of enzyme reduction was seen in the animals injected with $FeTPPS_4$ intravenously prior to sacrifice as compared to the animals not injected (64% vs 58% for CPK and 65% vs 56% for LDH).

Mitochondria contain a large amount of paramagnetic and ferromagnetic components including iron. A high intensity constant strength magnetic field would have a marked effect on mitochondrial function (i.e. oxidative phosphorylation as well as membrane activity both cellular and nuclear). The preservation of mitochondria and the maintenance of integrity of the cristae with a decrease in mitochondria edema formation is marked with the use of the high intensity constant strength magnetic field. In this study the intravenous injection of $FeTPPS_4$ particles was used to help augment the mitochondrial magnetic components prior to treatment. In this study slight improvement was evident with the use of the injection of particles prior to treatment.

Extension is possible to other tissues such as renal tissue during kidney transplantation and for Central Nervous System preservation. This new approach described above shows great potential either alone or in conjunction with present modalities.

What is claimed is:

1. A process for improvement and enhancement of transplantation comprising:
   (a) introducing particles not greater than about 1 micron into tissue selected from the group consisting of donor tissue, host tissue and combinations thereof, wherein the particles are selected from the group consisting of ferromagnetic, paramagnetic, and diamagnetic particles;
   (b) allowing time sufficient to promote intracellular accumulation and compartmentalization of said particles;
   (c) subjecting the tissue to an alternating electromagnetic field to inductively heat the particles; and
   (d) allowing time sufficient to inhibit or destroy cells in the tissue wherein said cells mediate the immunological response of rejection.

2. The process of claim 1 wherein the method of introduction of the particles is selected from the group consisting of intravenous injection, intra-arterial injection, intra-lymphatic injection, local perfusion and any combination thereof.

3. The process of claim 1 or 2 wherein the tissue is the host tissue prior to receiving the transplant.

4. The process of claim 1 or 2 wherein the tissue is the donor tissue prior to being transplanted.

5. The process of claim 1 or 2 wherein the tissue is both the donor tissue and host tissue after transplantation.

6. The process of claim 1 wherein the particles are introduced after transplantation when an episode of rejection at a local area has occurred.

7. The process of claim 6 further comprising the step of using a localized magnetic field to help guide the particles to the local area of rejection.

8. The process of claim 1 wherein the particles are characterized by a magnetic susceptibility greater than about $10^6$ cgs.

9. The process of claim 1 wherein the electromagnetic field is characterized by a field strength range of 300 gauss to 100 kilogauss.

10. The process of claim 9 wherein the particles are selected from the group consisting of elements, inorganic compounds, organic compounds and combinations thereof.

11. The process of claim 10 wherein said elements and inorganic compounds are selected from the group consisting of cobalt, zinc, chromium, iron, nickel, platinum, rare earth metals such as dysprosium, erbium, europium, gadolinium, holmium, samarium, terbium, thulium, ytterbium, yttrium and compounds and complexes thereof such as dysprosium sulfate, erbium sulfate, europium oxide, europium sulfate, gadolinium oxide, gadolinium sulfate, homium oxide, ferric oxide, ferric hydroxide, samarium sulfate, terbium sulfate, thulium oxide, ytterbium sulfide, yttrium oxide, yttrium sulfate, yttrium ferrioxide ($Y_3Fe_5O_{12}$), yttrium aluminum oxide ($Y_3Al_5O_{12}$), dysprosium-nickel, dysprosium cobalt, gadolinium-iron, ytterbium-iron, cobalt-samarium, gadolinium-ytterium, dysprosium-gallium, and actinide series elements and compounds and complexes thereof.

12. The process of claim 10 wherein said organic compounds are selected from the group consisting of
   (a) dextran metal complexes wherein said metal is selected from the group consisting of cobalt, zinc, chromium, gallium, manganese, nickel, platinum, dysprosium, erbium, europium, gadolinium, holmium, iron, samarium, terbium, thulium, ytterbium, yttrium, dysprosium-nickel, dysprosium-cobalt, gadolinium-iron, ytterbium-iron cobalt-samarium, gadolinium-yttrium, and dysprosium-gallium, and iron such as FeOOH-dextran complexes;
   (b) iron transporting and chelating compounds comprising ferric ammonium citrate, enterochelin, hydroxamates, phenolates, ferrichromes, desferri-ferrichromes, ferritin, ferric mycobactins and iron sulfur proteins such as ferredoxin and rubredoxin, as well as transferrin and transferrin compounds and complexes;
   (c) porphyrins comprising etioporphyrins, mesoporphyrins, uroporphyrins, coproporphyrins, protoporphyrins, dicarboxylic acid containing porphyrins, substituted porphyrins such as tetraphenylporphyrin sulfonate (TPPS and protoporphyrin containing molecules such as hematoporphyrins, chlorophylls, and cytochromes, as well as mixed-metal or di-metal hybrid porphyrins, and porphyrin-dextran complexes; and
   (d) metal complexes selected from the group consisting of metalloporphyrin-transferrin, antibody-ferritin-particles, antibody-ferritin-transferrin-particles, antibody-transferrin-particles, metal-porphyrin-metal complexes, metallothionein particles, and lectin particles.

13. The process of claim 10 wherein the natural occurring metal moiety of said porphyrin is optionally substituted with a metal selected from the group consisting of cobalt, zinc, chromium, gallium, manganese, nickel, platinium, dysprosium, erbium, europium, gadolinium, holmium, samarium, terbium, thulium, ytterbium, yttrium, dysprosium-nickel, dysprosium-cobalt, gadolinium-iron, ytterbium-iron, cobalt-samarium, gadolinium-yttrium, and dysporsium-gallium.

14. The process of claim 12 wherein said iron transporting, iron chelating and porphyrin compounds are chemically complexed with dextran.

15. The process of claim 13 wherein said compounds are chemically complexed with dextran.

16. The process of claim 1 wherein the magnetic qualities of the ferromagnetic, paramagnetic or diamagnetic particles in the tissue are used as a monitor of the state of the rejection process.

17. The process of claim 1 wherein the magnetic field is used in conjunction with a known tissue preservation technique selected from the group consisting of local cooling, vascular cooling, pharmacologic preservation, pulsatile perfusion and combinations thereof.

18. A process for improvement and enhancement of transplantation comprising:
   (a) introducing particles not greater than about 1 micron into tissue selected from the group consisting of donor tissue, host tissue and combinations thereof, wherein the particles are selected from the group consisting of ferromagnetic, paramagnetic, and diamagnetic particles;

(b) allowing time sufficient to promote intracellular accumulation and compartmentalization of said particles;

(c) subjecting the tissue to a constant electromagnetic field.

19. The process of claim 18 wherein the method of introduction of the particles is selected from the group consisting of intravenous injection, intra-arterial injection, intra-lymphatic injection, local perfusion and any combination thereof.

20. The process of claim 18 or 19 wherein the tissue is the host tissue prior to receiving the transplant.

21. The process of claim 18 or 19 wherein the tissue is the donor tissue prior to being transplanted.

22. The process of claim 18 or 19 wherein the tissue is both the donor tissue and host tissue after transplantation.

23. The process of claim 18 wherein the particles are introduced after transplantation when an episode of rejection at a local area has occurred.

24. The process of claim 23 further comprising the step of using a localized magnetic field to help guide the particles to the local area of rejection.

25. The process of claim 18 wherein the particles are characterized by a magnetic susceptibility greater than about $10^6$ cgs.

26. The process of claim 18 wherein the electromagnetic field is characterized by a field strength range of 300 gauss to 100 kilogauss.

27. The process of claim 18 or 26 wherein the particles are selected from the group consisting of elements, inorganic compounds, organic compounds and combinations thereof.

28. The process of claim 27 wherein said elements and inorganic compounds are selected from the group consisting of cobalt, zinc, chromium, iron, nickel, platinum, rare earth metals such as dysprosium, erbium, europium, gadolinium, holmium, samarium, terbium, thulium, ytterbium, yttrium and compounds and complexes thereof such as dysprosium sulfate, erbium sulfate, europium oxide, europium sulfate, gadolinium oxide, gadolinium sulfate, homium oxide, ferric oxide, ferric hydroxide, samarium sulfate, terbium sulfate, thulium oxide, ytterbium sulfide, yttrium oxide, yttrium sulfate, yttrium ferrioxide ($Y_3Fe_5O_{12}$), yttrium aluminum oxide ($Y_3Al_5O_{12}$), dysprosium-nickel, dysprosium cobalt, gadolinium-iron, ytterbium-iron, cobalt-samarium, gadolinium-ytterium, dysprosium-gallium, and actinide series elements and compounds and complexes thereof.

29. The process of claim 27 wherein said organic compounds are selected from the group consisting of (a) dextran metal complexes wherein said metal is selected from the group consisting of cobalt, zinc, chromium, gallium, manganese, nickel, platinum, dysprosium, erbium, europium, gadolinium, holmium, iron, samarium, terbium, thulium, ytterbium, yttrium, dysprosium-nickel, dysprosium-cobalt, gadolinium-iron, ytterbium-iron cobalt-samarium, gadolinium-yttrium, and dysprosium-gallium, and iron such as FeOOH-dextran complexes;

(b) iron transporting and chelating compounds comprising ferric ammonium citrate, enterochelin, hydroxamates, phenolates, ferrichromes, desferri-ferrichromes, ferritin, ferric mycobactins and iron sulfur proteins such as ferredoxin and rubredoxin, as well as transferrin and transferrin compounds and complexes;

(c) porphyrins comprising etioporphyrins, mesoporphyrins, uroporphyrins, coproporphyrins, protoporphyrins, dicarboxylic acid containing porphyrins, substituted porphyrins such as tetraphenylporphyrin sulfonate (TPPS and protoporphyrin containing molecules such as hematoporphyrins, chlorophylls, and cytochromes, as well as mixed-metal or di-metal hybrid porphyrins, and porphyrin-dextran complexes; and (d) metal complexes selected from the group consisting of metalloporphyrin-transferrin, antibody-ferritin-particles, antibody-ferritin-transferrin-particles, antibody-transferrin-particles, metal-porphyrin-metal complexes, metallothionein particles, and lectin particles.

30. The process of claim 29 wherein said iron transporting, iron chelating and porphyrin compounds are chemically complexed with dextran.

31. The process of claim 27 wherein the natural occurring metal moiety of said porphyrin is optionally substituted with a metal selected from the group consisting of cobalt, zinc, chromium, gallium, manganese, nickel, platinum, dysprosium, erbium, europium, gadolinium, holmium, samarium, terbium, thulium, ytterbium, yttrium, dysprosium-nickel, dysprosium-cobalt, gadolinium-iron, ytterbium-iron, cobalt-samarium, gadolinium-yttrium, and dysporsium-gallium.

32. The process of claim 31 wherein said compounds are chemically complexed with dextran.

* * * * *